United States Patent [19]

Coughlin et al.

[11] Patent Number: 5,231,003
[45] Date of Patent: Jul. 27, 1993

[54] **MONOCLONAL ANTIBODIES SPECIFIC FOR TOXIN B OF *CLOSTRIDIUM DIFFICILE***

[75] Inventors: Richard T. Coughlin, Leicester; Dante J. Marciani, Hopkinton, both of Mass.

[73] Assignee: Cambridge Bioscience Corporation, Worcester, Mass.

[21] Appl. No.: 522,881

[22] Filed: May 11, 1990

[51] Int. Cl.$^5$ ............... G01N 33/569; G01N 33/577; C12N 5/00; C07K 15/28
[52] U.S. Cl. .................. 435/7.32; 435/7.92; 435/240.27; 436/548; 530/388.4; 530/391.3
[58] Field of Search .............. 435/7.32, 7.92, 7.94, 435/172.2, 240.27, 842; 436/518, 528, 548; 530/387, 388.4, 391.1, 391.3

[56] References Cited

U.S. PATENT DOCUMENTS 4,533,630  8/1985  Wilkins et al. ............. 435/7.32
4,879,218  11/1989  Wilkins et al. ............. 435/7.32

FOREIGN PATENT DOCUMENTS 0154064  3/1984  European Pat. Off. .

OTHER PUBLICATIONS

Sevier et al, Clin. Chem 27(11):1797–1806 (1981).
Bartlett, John G., *Clinics in Gastroenterology* 8(3):783–801 (1979).
Trnka, Yvona M., et al., *Gastroenterology* 80(4):693–696 (1981).
Sullivan, N. M. et al., *Infection and Immunity* 35(3):1032–1040 (1982).
Rothman, Sara W. et al., *Infection and Immunity* 46(2):324–331 (1984).
Lyerly, David M., et al., *Journal of Clinical Microbiology* 26(3):397–400 (1988).
Peterson, Lance R. et al., *Am. J. Clin. Path.* 87:298–299 (1987).
Walker, Randall C., et al., *Diagn Microbiol. Infect. Dis* 5:61–69 (1986).
Lyerly, David M., et al., *Infection and Immunity* 54(1):70–76 (1987).
Popoff, Michael R., *Infection and Immunity* 55(1):35–43 (1987).
Chang, Te-Wen, et al., *Infection and Immunity* 22(2):418–422 (1978).
Lyerly, David M., et al., *FEMS Microbiology Letters* 33:31–35 (1986).
Libby, Jeffrey M., et al., *Infection and Immunity* 35(1):374–376 (1982).
Rolfe, Rial D., et al., *Infection and Immunity* 25(1):191–201 (1979).
Laughon, Barbara E., et al., *The Journal of Infectious Diseases* 149(5):781–788 (1984).
Banno, Yoshiko, *Biochemistry International* 2(6):629–635 (1981).

*Primary Examiner*—Mary E. Ceperley
*Assistant Examiner*—Carol E. Bidwell
*Attorney, Agent, or Firm*—Sterne, Kessler, Goldstein & Fox

[57] ABSTRACT

Monoclonal antibodies specific for Toxin B of *Clostridium difficile* are provided. Further, methods for making and using the antibodies are given, particularly the use of the antibodies for the detection of *C. difficile*.

9 Claims, 2 Drawing Sheets

MONOCLONAL ANTIBODIES SPECIFIC FOR TOXIN B OF *CLOSTRIDIUM DIFFICILE*

BACKGROUND OF THE INVENTION

*Clostridium difficile* is the major cause (95%) of disease in patients suffering from antibiotic-associated pseudomembranous colitis and is moderately associated (20%) with patients having antibiotic-associated diarrhea without colitis (Bartlett, J., *Clin Gastroenterol.* 8:783-801 (1979)). In addition, 19% of patients with chronic inflammatory bowel disease have the *C. difficile* toxin in their stools and a positive correlation exists between the severity of the illness and the presence of toxin (Trnka, Y., et al., *Gastroenterology* 80:693-696 (1981)).

There are two toxins, Toxin A and Toxin B, produced by *C. difficile* (Sullivan, N. M., *Infect. Immun.* 33:1032-1040 (1982)). Toxin A, or enterotoxin, is responsible for the increase in intestinal permeability associated with disease (Triadafilopoulos, G., et al., *Gastroenterology* 93:273-279 (1987)). Toxin B, or cytotoxin, is a thousand-fold more potent than Toxin A in triggering the cytotoxic effect in cultured cells (Rothman, S. W., *Infect. Immun.* 46:324-331 (1984); Sullivan, N. M., *Infect. Immun.* 33:1032-1040 (1982)).

Toxin A has been reported to have a molecular weight greater than 300,000 kDa while Toxin B is slightly smaller (Lyerly, D. H., et al., *Infect. Immun.* 54:70-76 (1986)). Further, antisera made against one toxin is not cross-reactive with the other. Thus, the two toxins have distinct biological and serological activity.

Although specific antibiotic therapy exists, a rapid and accurate diagnostic assay for the toxins responsible for the disease does not exist. A rapid latex test has been developed, however, it detects a 43,000 molecular weight *C. difficile* associated protein (Lyerly, D. M., et al., *J. Clin. Microbiol.* 26:397-400 (1988)) that is only weakly (67%) associated with clinically defined disease (Peterson, L. R., *Am. J. Clin. Path.* 87:298-299 (1987)). The in vitro cell cytotoxicity assay is a widely accepted diagnostic for *C. difficile* associated disease. Unfortunately, this test requires 48 hours to perform and requires technicians skilled in tissue culture. The performance of toxin specific polyclonal based EIA have been disappointing. This is because of the relatively low toxin specific titer and the high level of nonspecific reactivity of the polyclonal antisera (Walter, R. C., et al., *Diagn. Microbiol. Infect. Dis.* 5:61-69 (1986)).

Despite their potential utility in the detection of disease, the generation of toxin-specific hybridomas has proven difficult. Lyerly et al., supra. report the production of Toxin A specific monoclonal antibodies. Also, Wilkins et al. in U.S. Pat. No. 4,879,218, issued Nov. 7, 1989, describe the production of Toxin A specific monoclonal antibodies. This patent also describes the production of mono-specific Toxin B antibodies made from polyclonal serum containing both Toxin A and Toxin B antibodies.

A need continues to exist for Toxin B monoclonal antibodies, without cross reactivity to Toxin A of *C. difficile*.

SUMMARY OF THE INVENTION

The present invention is drawn to antibodies, particularly monoclonal antibodies specific for Toxin B of *Clostridium difficile*. The antibodies show no reactivity to Toxin A from *C. difficile*. The antibodies are useful in methods for the detection and treatment of Clostridium.

DESCRIPTION OF THE PREFERRED EMBODIMENTS

Figure 1A:
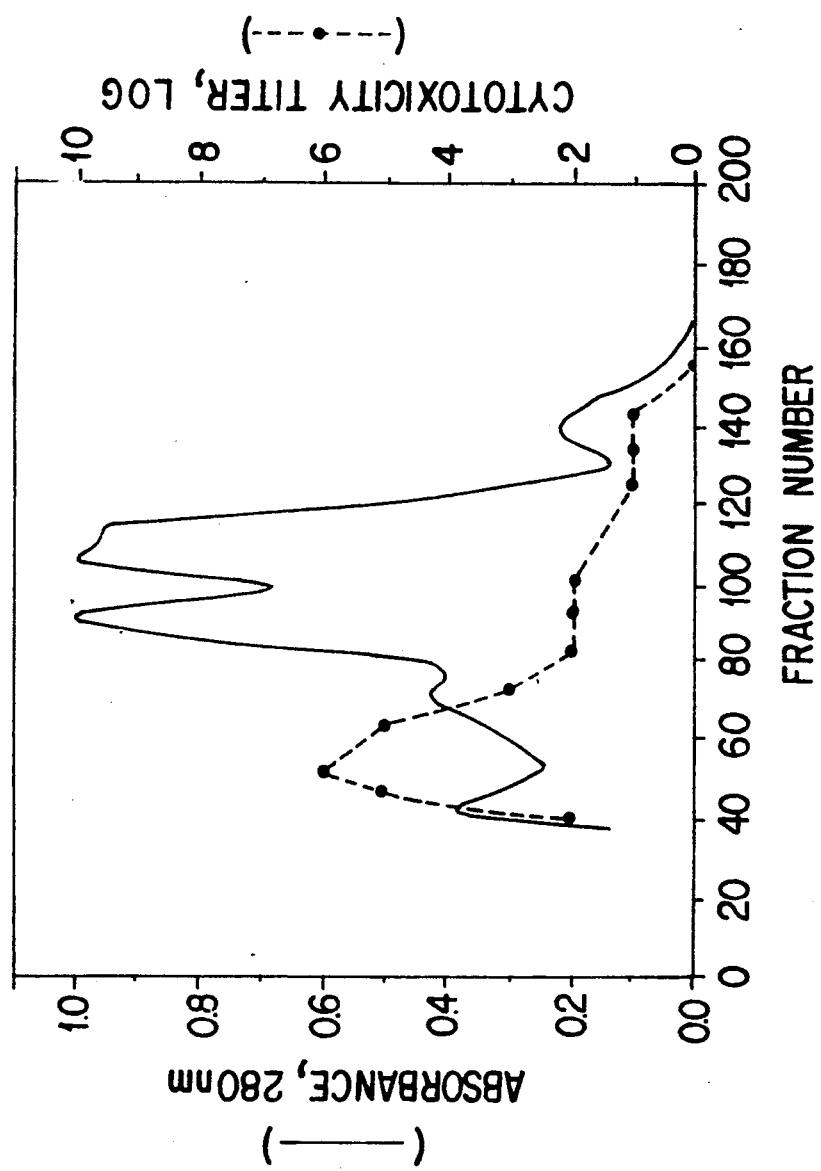
FIG. 1A AND 1B: Purification of Toxin B by gel permeation and anion exchange chromatography. A) Concentrated *C. difficile* 10463 cell culture supernatant fractionated on a 5-300 column. B) Cytotoxin rich pooled fractions from the 5-300 column eluted from a DEAE column.

Compositions and Methods for the Detection and Treatment of Enterocolitis Caused by *C. difficile*

Monoclonal antibodies are provided which are specific for Toxin B of *C. difficile*. The antibodies find use in assays for the detection of *C. difficile* and in therapies for the treatment of enterocolitis.

The monoclonal antibodies of the present invention are specific for Toxin B of *C. difficile*. The antibodies react with a 250 kDa protein and the supernatants of toxigenic *C. difficile* and are unreactive with nontoxigenic *C. difficile* strains. The monoclonal antibodies do not react with concentrated supernatants from *C. sordellii*, *C. bifermentans*, *C. perfingens*, or the purified Toxin A from *C. difficile*. This is in direct contrast to the results which have been demonstrated utilizing polyclonal antisera developed against Toxin B. Polyclonal antisera developed against Toxin B reacted strongly with supernatants from *C. sordellii*, *C. bifermentans* and the nontoxigenic strain 2037.

As is generally known in the art, antibodies are deemed to be cross reactive when it binds with an antigen other than the one used to elicit formation of that antibody. By the present invention, the antibodies against Toxin B do not cross react with Toxin A.

The antibodies of the present invention are prepared by immunization of an animal, such as a rabbit, with inactive Toxin B antigens. A specific method is set forth in the experimental section which provides for the recovery of Toxin B rich fractions.

After purification of the toxin, Toxin B can be inactivated utilizing several methods. For example, the toxin can be inactivated utilizing SDS or alternatively by utilizing formaldehyde. Both these methods are set forth in more detail in the experimental sections. The inactivated toxins may be utilized to immunize animals for the production of monoclonal antibodies.

It is of particular importance that the monoclonal antibodies of the present invention do not cross react with Toxin A. While it can only be hypothesized why the specific protocol of the present invention is capable of preparing monoclonal antibodies specific for Toxin B, it is recognized that this capability may be specific to a single aspect of the experimental scheme. For example, it is possible that the purification methods set forth in the experimental section provides highly purified Toxin B which could be utilized in other methodologies for the production of monoclonal antibodies. Alternatively, the inactivation means provided in the present application may have provided inactivated Toxin B with less cytotoxic effects such that the stimulated B cells were capable of producing antibodies. It is in recognition that the highly purified inactivated Toxin B of the present invention is capable of producing monoclonal antibodies that a general description of monoclonal antibody production is provided.

For the most part, various methodologies are well known in the art of immunology for the production of monoclonal antibodies. Standard reference works setting forth the general principles of immunology include the work of Klein, J. (*Immunology: The Science of Cell-Noncell Discrimination*, John Wiley & Sons, New York (1982)); Kennett, R., et al. (*Monoclonal Antibodies, Hybridoma: A New Dimension in Biological Analyses*, Plenum Press, New York (1980)); Campbell, A. ("Monoclonal Antibody Technology," In: *Laboratory Techniques in Biochemistry and Molecular Biology*, Volume 13 (Burdon, R., et al., eds.), Elsevier, Amsterdam (1984)); and Eisen, H. N., (In: *Microbiology*, 3rd Ed. (Davis, B. D., et al., Harper & Row, Philadelphia (1980)).

The monoclonal antibodies of the invention may be "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al.. European Patent Application 125,023; Better, M. et al., *Science* 240:1041-1043 (1988); Liu, A. Y. et al., *Proc. Natl. Acad. Sci. USA* 84:3439-3443 (1987); Liu, A. Y. et al., *J. Immunol.* 139:3521-3526 (1987); Sun, L. K. et al *Proc. Natl. Acad. Sci. USA* 84:214-218 (1987); Nishimura, Y. et al., *Canc. Res.* 47:999-1005 (1987); Wood, C. R. et al., *Nature* 314:446-449 (1985)); Shaw et al., *J. Natl. Cancer Inst.* 80 1553-1559 (1988).

General reviews of "humanized" chimeric antibodies are provided by Morrison, S. L. (*Science.* 229:1202-1207 (1985)) and by Oi, V. T. et al., *BioTechniques* 4:214 (1986)).

Suitable "humanized" antibodies can be alternatively produced by CDR or CEA substitution (Jones, P. T. et al., *Nature* 321:552-525 (1986); Verhoeyan et al., *Science* 239:1534 (1988); Beidler, C. B. et al., *J. Immunol.* 141:4053-4060 (1988)).

An antibody is said to be "capable of binding" a molecule if it is capable of specifically reacting with the molecule to thereby bind the molecule to the antibody. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')2 fragments) which are capable of binding hapten. Fab and F(ab')2 fragments lack the Fc fragment of intact antibody, clear more rapidly from the ciruclation, and may have less non-specific tissue binding of an intact antibody (Wahl et at., *J. Nucl. Med.* 24:316-325 (1983)). It will be appreciated that Fab and F(ab')2 and other fragments of the antibody of the present invention may be used according to the methods of the present invention for the detection and treatment of colon adenocarcinoma in the same manner as intact antibody. Such fragments are typically produced by proteolytic cleavage, such as papain (to produce Fab fragments) or pepsin (to produce F(ab')2 fragments). Alternatively, hapten-binding fragments can be produced through the application of recombinant DNA technology or through synthetic chemistry.

Monoclonal antibodies are prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563-681 (1981)). In general, such procedures involve immunizing an animal with inactive purified Toxin B. The splenocytes of such animal are extracted and fused with a suitable myeloma cell line. Any suitable myeloma cell line may be employed in accordance with the present invention; however, it is preferable to employ the parent myeloma cell line ($SP_2O$), available from the American Type Culture Collection, Rockville, Md. After fusion, the resulting hybridoma cells are selectively maintained in HAT medium, and then cloned by limiting dilution as described Wands, J.R., et al., *Gastroenterology* 80:225–232 (1981), which reference is herein incorporated by reference). The hybridoma cells obtained through this selection are then assayed to identify clones which secrete antibodies specific for Toxin B. The preferred hybridoma cell lines are 5AB and 5A2.

Through application of the above-described methods, additional cell lines capable of producing antibodies specific for Toxin B can be obtained.

Alternatively, additional antibodies may be produced in a two-step procedure through the use of anti-idiotypic antibodies. Such a method makes use of the fact that antibodies are themselves haptens, and that, therefore, it is possible to obtain an antibody which binds to a second antibody. In accordance with this method, antibodies capable of binding Toxin B are used to immunize an animal. The splenocytes of such an animal are then used to produce hybridoma cells, and the hybridoma cells are screened to identify clones which produce antibody capable of binding antibody to Toxin B. Such antibodies comprise anti-idiotypic antibodies. Such antibodies can be used to immunize an animal, and thereby induce the formation of anti-Toxin B antibodies. Hence, antiidiotypic antibodies provide one method for inducing, or enhancing, an animal's immune response.

The antibodies (or fragments thereof) of the present invention are particularly suited for use in immunoassays wherein they may be utilized in liquid phase or bound to a solid-phase carrier.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, betagalactosidase, ribonuclease, urease, catalase, glucose-6-phosphate dehydrogenase, glucoamylase, acetylcholine esterase, etc.

Examples of suitable radioisotopic labels include $^{3}H$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$ , $^{211}At$, $^{212}Pb$, $^{47}Sc$, and $^{109}Pd$.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1–31 (1976)), and Schurs, A. H. W. M., et al. (Clin. Chim. Acta 81:1–40 (1977)). Coupling techniques mentioned in the latter are the glutaraldehyde method, the periodate method, the dimaleimide method, the m-maleimidobenzyl-N-hydroxy-succinimide ester method, all these methods incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. Those skilled in the art will note many other suitable carriers for binding monoclonal antibody, or will be able to ascertain the same by use of routine experimentation.

The antibodies, or fragments of antibodies, of the present invention may be used to quantitatively or qualitatively detect the presence of Toxin B antigen. Such detection may be accomplished using any of a variety of immunoassays. For example, by radioactively labeling the antibodies or antibody fragments, it is possible to detect SF-25 antigen through the use of radioimmune assays. A good description of a radioimmune assay (RIA) may be found in laboratory techniques and biochemistry in molecular biology, by Work, T. S., et al., North Holland Publishing Company, NY (1978), with particular reference to the chapter entitled "An Introduction to Radioimmune Assay and Related Techniques" by Chard, T., incorporated by reference herein.

The binding molecules of the present invention may also be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, lymph, liquified stools, tissue homogenate, etc.) and the quantity of soluble antibody bearing the label that permits detection and/or quantitation of the ternary complex formed between solid-phase antibody, antigen, and labeled antibody is added.

Typical immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody. After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. These "two-site" or "sandwich" assays are described by Wide at pages 199–206 of *Radioimmune Assay Method.* edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplex labeled antibody. The presence of labeled antibody associated with the solid support is then determined as it would be in a conventional "forward" sandwich assay.

In the reverse assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the simultaneous and forward assays.

As explained above, the immunometric assays for antigen require that the particular binding molecule be labeled with a "reporter molecule." These reporter molecules or labels, as identified above, are conventional and well-known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, betagalactosidase, urease, glucose oxidase, glycoamylase, malate dehydrogenase, and glucose-6-phosphate dehydrogenase. Urease is among the more preferred enzyme labels, particularly because of chromogenic pH indicators which make its activity readily visible to the naked eye.

As used herein, an effective amount of a diagnostic reagent (such as an antibody, antibody fragment, or a hapten) is one capable of achieving the desired diagnostic discrimination. The amount of such materials which are typically used in a diagnostic test are generally between 0.1-1 micron g, and preferably between 0.1-1 micron g.

In addition to providing a method for diagnosing colitis, the present invention also provides a means for preventing and for treating enterocolitis.

EXPERIMENTAL

Figure 1B:
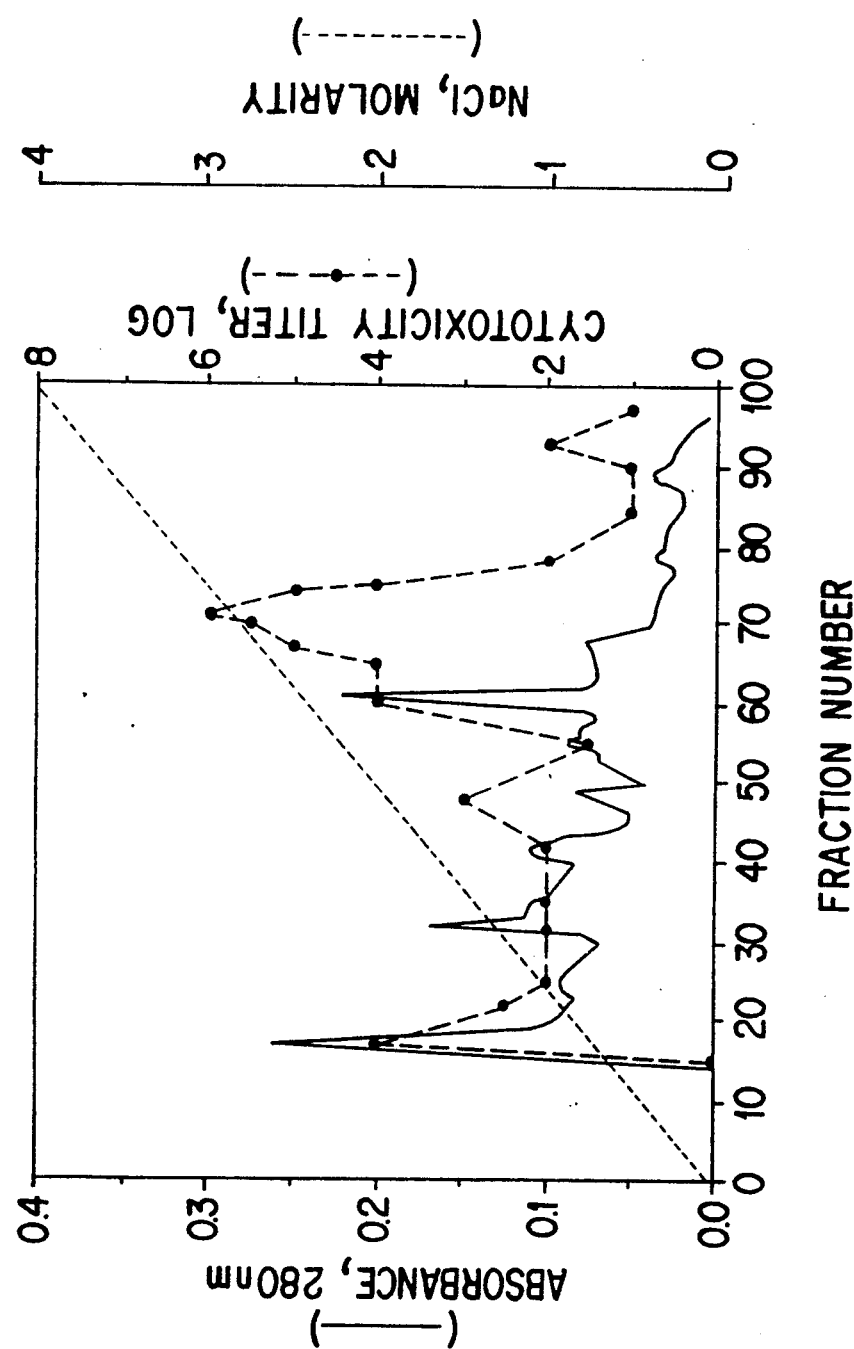

Bacterial strains and growth conditions. The toxigenic strain 10463 and the nontoxigenic strain 2037 of *C. difficile* as well as *C. sordellii, C. bifermentans* and *C. perfringens* were the generous gifts of Dr. Thomas LaMont (University Hospital, Boston, Mass.). Cells were grown anaerobically in Brain Heart Infusion Broth (Scott Laboratories, Carson, Calif.) at 37° C. until stationary phase was reached.

Toxin purification. 400 ml of bacterial supernatant was either concentrated 25 fold on a YM-30 membrane (Amicon Corp., Danvers, Mass.) or precipitated using 70% ammonium sulfate. The concentrated supernatant was then fractionated on a 90×2.5 cm column of Sephacryl-300 (Pharmacia-LKB, Piscataway, N.J.). The pooled toxin containing fractions were then applied to a superfine DEAE-TSK column (Toyo Soya, Japan) attached to a Waters 650 Advanced Protein Purification System (Millipore, Bedford, Mass.). The sample was loaded in 50 mM Tris, pH 8.0 and eluted in 90 mM Tris, 1M NaCl, pH 8.0. In all cases, Toxin B rich column fractions were identified by the cytotoxicity assay. The efficiency of recovery as judged by cytotoxicity was 20% after anion exchange. Toxin A was purified by the method of Sullivan et al. (Sullivan, N. M., *Infect. Immun.* 33:1032-1040 (1982)).

Toxin B was inactivated using two methods. SDS inactivated Toxin B was generated using 100 ug/ml of Toxin B in 0.5% sodium dodecyl sulphate and heating at 100° C. for 90 seconds. Formaldehyde inactivated Toxin B was made by incubating 1 mg/ml of ToxinB with 0.4% formaldehyde at 37° C. for 36 hours.

Immunization of animals and generation of hybridoma cell lines. A 5 pound female New Zealand White rabbit, R460, was injected intradermally on days 0, 21, 42, 63, 90, 117 and 144 with 100 ug of formaldehyde inactivated Toxin B. The first immunization was in complete Freund's adjuvant while all subsequent injections were in incomplete Freund's adjuvant. Serum was collected one week after the last immunization. Two additional rabbits, R458 and R459, were immunized using an identical schedule with 250 ug of formaldehyde inactivated crude Toxin B. Crude Toxin B represents material that had not been purified to near homogeneity by DEAE chromatography.

Female RBF/DnJ mice were obtained from Jackson Laboratories (Bar Harbor, ME). The mice were immunized on day 0 intradermally with 5 ug of SDS inactivated Toxin B in complete Freund's adjuvant, on day 19 intraperitoneally with 5 ug of SDS inactivated Toxin B in incomplete Freund's adjuvant, on day 30 intraperitoneally with 5 ug of SDS inactivated Toxin B, on day 42 intraperitoneally with 2 ug SDS inactivated Toxin B, on day 55 intravenously with 2 ug of heat inactivated Toxin B, and on day 127 intraperitoneally with 1 ug of heat inactivated Toxin B, and on day 128 intravenously with 1 ug of heat inactivated Toxin B. On day 130, a fusion was done on cells derived from lymph nodes and spleen.

Fusion screening. The hybridomas were screened for their ability to capture Toxin B in an EIA format. Briefly, Immulon I plates (Fisher, Boston, MA) were coated with 100 ul of 2.8 ug/ml goat anti-mouse IgG (heavy and light chain) (Boehringer Mannheim Biochemicals, Indianapolis, Ind.) in water. 100 ul of 0.005% glutaraldehyde was then added and the plates were left at room temperature overnight. Plates were then washed once with 10 mM sodium phosphate pH 7.2 with 0.1% sodium azide. Plates were then blocked with 200 ul of 4% bovine serum albumin in 10 mM sodium phosphate with azide overnight. Blocked plates were then overlaid with 200 ul of 2.5% sucrose in 10 mM sodium phosphate with azide overnight. Plates were then air dried and stored at 4° C. in a desiccated pouch.

100 ul of tissue culture supernatant diluted 1:10 in 50 mM Tris HCl, pH 7.6, 50% heat inactivated calf serum, 0.05% Tween 20, 0.02% thimerosal, and 0.0016% gentamicin was added to each well for 1 hour at room temperature. Plates were then washed five times with 200 ul of 0.05% Tween 20. Plates were then incubated for one hour at room temperature with 500 ng/ml of Toxin B in fetal calf serum diluent. Plates were then washed five times with 0.05% Tween 20 and then overlaid with 100 ul HRP conjugated to antisera developed against crude Toxin B. Plates were then washed five more times with 0.05% Tween 20 and developed with $TMB/H_2O_2$.

Direct EIA. 96 well Immulon I plates were coated with 100 ul of tissue culture supernatants of either *C. difficile* 10463, or 2037, *C. sordellii, C. bifermentans,* or *C. perfringens* overnight at room temperature. Plates were then blocked with 4% bovine serum albumin in phosphate buffered saline, 0.1% sodium azide, pH 7.0 overnight at room temperature. 100 ul of hybridoma tissue culture supernatant diluted 1:10 or rabbit sera diluted at 1:5000 in BSA-PBS was then added to each well and incubated for two hours at room temperature. Plates were then washed five times with PBS followed by the addition of 100 ul of 1:5000 dilution of HRP conjugated to either goat anti-mouse Ig (heavy and light chain) or antirabbit (IgG $F(ab')_2$) in BSA-PBS for one hour. After five more 200 ul washes with PBS the wells were developed as before.

Miscellaneous methods. Isotyping reagents were obtained from Southern Biotechnology Associates, Inc. (Birmingham, Ala.). Toxin containing samples were subjected to sodium dodecyl sulfate polyacrylamide gel electrophoresis (SDS-PAGE). Samples were electrophoretically transferred to nitrocellulose and immunostained using either neat hybridoma tissue culture supernatants or polyclonal antisera diluted 1:1000 into BSA-PBS. Detection was accomplished using HRP conjugated to either goat anti-mouse IgG (heavy and light chain) or anti-rabbit IgG F(ab')2 with minimum cross reactivity to human serum proteins (Pel Freez, Rogers, Ark.). 4-chloro-l-naphthol was used to develop specific antibody. A cytotoxicity assay was performed on human newborn foreskin diploid fibroblasts obtained from Bartell Immunodiagnostics (Bellevue, Washington). Samples were judged to be positive for cytotoxicity after 48 hours if they produced cell rounding that was inhibitable by anti-toxin sera.

RESULTS

Purification of antigens. Toxin B purification was accomplished by concentration, size exclusion chromatography, and anion exchange chromatography. There was virtually no loss of cytotoxicity after concentration. FIG. 1A shows a typical fractionation of concentrated bacterial supernatant by gel chromatography. In this case, fractions 44 through 66 were pooled. This step had a 60% efficiency of cytotoxin recovery. FIG. 1B shows an elution profile of 5-300 purified material from a DEAE column. Fractions 63-75 were pooled. Although Coomassie blue stained gels of DEAE purified Toxin B showed that the protein was nearly homogeneous, less than 10% of the initial cytotoxicity was recovered.

Hybridomas. Of 886 fusion wells plated, 502 were positive for growth, and 213 wells produced antibody which were reactive in Toxin B capture assay. Six wells were cloned and expanded for subsequent analysis. Similar fusions resulted in a much lower percentage of specific wells. Hybridomas derived from those fusions frequently produced antibodies which reacted with minor low molecular weight non-Toxin B contaminants in Western blot.

Direct EIA. In a direct EIA tissue culture, supernatants from all six monoclonal antibodies reacted strongly with both purified Toxin B and supernatants from the toxigenic *C. difficile* strain 10463 (Table 1). None of the monoclonal antibodies tested reacted with either purified Toxin A or supernatants from *C. sordellii*, *C. bifermentans*, *C. perfringens*, or the nontoxigenic *C. difficile* strain 2037. In sharp contrast, all of the polyclonal antisera cross reacted with C. sordellii and bifermentans as well as the nontoxigenic *C. difficile* strain 2037. The degree of cross reactivity was variable and independent of antigen purity. None of the polyclonal antisera were reactive with either Toxin A or *C. perfringens*. Pre-immune sera from these rabbits were unreactive with any of the antigens tested.

*C. sordellii* were precipitated with 70% ammonium sulfate, resuspended in 0.1M Tris, pH 8.0, and desalted on a Sephadex G-2 5 column that had been pre-equilibrated with 20 mM Tris-HCl, pH 8.0. Undigested *C. difficile* or *C. sordellii* proteins were compared. *C. difficile* or *C. sordellii* proteins were digested for 30 minutes at 37° C. with trypsin at a 1:50 weight ratio of enzyme to bacterial protein. (Results not shown.) Although very antigenic, this material was substantially less cytotoxic than high molecular weight Toxin B (FIG. 1A) and could be removed by S-300 chromatography. A similar set of immunoreactive bands (60 and 250 kDa) could be seen in the concentrated cell culture supernatants of *C. sordellii* using the monoclonal antibodies 5A2 (not shown) and 5C8. The other monoclonal antibodies were completely unreactive with *C. sordellii* in Western blots. All of the immunoreactive bands were trypsin sensitive, however, they did not produce identical break down products. The lowest molecular weight immunoreactive trypsin fragment of *C. difficile* Toxin B was 50 kDa while the lowest molecular weight trypsin fragment of *C. difficile* was 79 kDa.

CONCLUSIONS

While Lyerly et al. *Infect. Immun.* 54:70-76 (1986) showed that one of their Toxin A specific monoclonal antibodies weakly cross reacted with Toxin B, none of the six Toxin B specific monoclonal antibodies cross reacted with Toxin A. Furthermore, the rabbit polyclonal antisera developed against purified Toxin B as disclosed herein was unreactive with pure Toxin A. This, of course, does not preclude the existence of conserved domains in the two toxins but does suggest that

TABLE 1

| Mab[a] | Isotype | Pure C. difficile | | c. difficile supernatant | | Supernatants from clostridium | | |
|---|---|---|---|---|---|---|---|---|
| | | Toxin A | Toxin B | 10463 | 2037 | sordellii | bifermentans | perfringens |
| 5A2 | IgG2b,k | 0.083 | 2.819 | 1.592 | 0.087 | 0.052 | 0.042 | 0.054 |
| 5C8 | IgM,k | 0.162 | 3.000 | 2.011 | 0.069 | 0.073 | 0.103 | 0.074 |
| 7D8 | IgG1,k | 0.063 | 1.837 | 0.777 | 0.033 | 0.033 | 0.037 | 0.043 |
| 5A8 | IgG1,k | 0.071 | 3.000 | 3.000 | 0.029 | 0.028 | 0.038 | 0.039 |
| 1D5 | IgG1,k | 0.131 | 3.000 | 3.000 | 0.062 | 0.052 | 0.064 | 0.173 |
| 1G6 | IgG1,k | 0.086 | 3.000 | 3.000 | 0.042 | 0.062 | 0.048 | 0.055 |
| Polyclonal[b] | | | | | | | | |
| R458 | NR | 0.057 | 2.108 | 3.000 | 0.977 | 1.077 | 0.966 | 0.137 |
| R459 | NR | 0.039 | 0.885 | 2.348 | 0.348 | 0.329 | 0.372 | 0.093 |
| R460 | NR | 0.050 | 2.457 | 1.362 | 1.752 | 1.247 | 0.908 | 0.079 |

[a]Using a 1:10 dilution of the indicated monoclonal antibody tissue culture supernatant and HRP conjugated goat anti-mouse Ig (heavy and light chain) for detection as described in the Materials and Methods section.
[b]Using a 1:5000 dilution of rabbit polyclonal antisera and HRP conjugated goat anti-rabbit IgG F(ab')2 with minimum cross reactivity to human servm proteins (Pel Freez, Rogers, AR).
MR = Not relevant.

Western blot analysis of *C. difficile* toxin. Western blot analysis was done in SDS-PAGE of, S-300 purified Toxin B with R460, R459, R458, 5C8, 5A2, 7D8, 1D5AB, and 1G6. Antisera was diluted 1:1000, while monoclonal antibodies were used as tissue culture supernants. All of the monoclonal antibodies and the polyclonal antisera were reactive with an identical band in the concentrated supernatant from the toxigenic *C. difficile* strain 10463 and in the purified Toxin B (results not shown). The polyclonal antisera also recognized major bands at 40 and 55 kDa with a minor set of triplet bands at approximately 100 kDa.

All of the Toxin B specific monoclonal antibodies also detected a variable amount of a 50 kDa protein which was present in the concentrated cell culture supernatants of *C. difficile*. Western blots were performed of Toxin B and *C. sordellii* following trypsin treatment. Cell culture supernatants of either *C. difficile* 10463 or these domains are not immunologically dominant.

Despite the rather high frequency of Toxin B specific hybridomas observed in this fusion, previous attempts were much less successful. The cytotoxic effects of Toxin B required the extreme procedures described herein to complete inactivation. Even with this precaution, mice were generally quite sick after immunization. A possible explanation is that denaturation of Toxin B was sufficiently harsh that stimulated B cells infrequently produced antibodies which recognized the native antigen used in the fusion screening process. In addition, many wells which scored positive in the direct Toxin B screening assay later proved to be reactive with heat stable minor proteins which contaminate the immunogen. Presumably these are the same proteins which are prominent in the Western blots of Toxin B developed using rabbit antisera to Toxin B.

Antisera to *C. sordellii* lethal toxin has been reported to cross react with Toxin B but not Toxin A of *C. difficile* (Popoff, M. R., Infect. Immun. 55:35–43 (1987)). Antisera to *C. sordellii* toxin has even been shown to neutralize *C. difficile* cytotoxicity (Chang, T. W., et al., *Infect. Immun.* 22:418–422 (1978)). None of the six monoclonal antibodies were reactive in a direct EIA with cell culture supernatant of *C. sordellii*. Two of the monoclonal antibodies, 5C8 and 5A2, did detect a high molecular weight protein in the Western blot of concentrated cell culture supernatants of *C. sordellii*. This protein like Toxin B was trypsin sensitive but did not produce immunoreactive fragments with the same molecular weight. None of the monoclonal antibodies detected this antigen in direct EIA. It is likely that differences in the expression level or the ability to coat plastic account for the lack of reactivity of any of the monoclonal antibodies with *C. sordellii* in direct EIA. It is also possible that the epitope recognized by these monoclonal antibodies is only exposed on denatured *C. sordellii* toxin. The present Toxin B specific rabbit antisera were reactive with *C. sordellii* and with *C. bifermentans* in direct EIA, but were unreactive with *C. perfringens*. Although some of this reactivity may have been due to conserved epitopes on Toxin B, other antigens in the cell culture supernatants may also contribute to the observed reactivity. This is supported by the strong direct EIA reactivity of the rabbit antisera with the nontoxigenic strain of *C. difficile*.

Results with the Toxin B specific polyclonal antisera are similar to those previously reported. The trace contaminants seen in Coomassie stained gels dominate the reactivity of antisera to concentrated supernatants of toxigenic *C. difficile* in Western blot. These contaminants are thus either highly immunogenic or relatively resistant to heat and detergent denaturation. None of the monoclonal antibodies described here are reactive with these bands and it is therefore unlikely that the lower molecular weight fragments are subunit products of high molecular weight Toxin B. It is the high level of reactivity with antigens other than toxin and the relatively low toxin specific titers of the Toxin B antibodies that have hindered the development of a reliable *C. difficile* diagnostic.

Preliminary evidence shows that these monoclonal antibodies will be useful in the detection of Toxin B in the stools of patients with *C. difficile* associated disease.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

DEPOSIT INFORMATION

Cell lines 5A8 and 5A2 were deposited with the American Type Culture Collection, Rockville, Md. on May 11, 1990 and given the designation ATCC No. HB10455 and ATCC No. HB10454, respectively.

What is claimed is:

1. A monoclonal antibody specific for Toxin B of *Clostridium difficile* which is not cross-reactive with Toxin A of *Clostridium difficile*.

2. The monoclonal antibody of claim 1 wherein the monoclonal antibody is produced from a hybridoma selected from the group consisting of 5C8, 5A2, 7D8, 5A8, and 1D5.

3. A hybridoma which produces a monoclonal antibody specific for Toxin B of *Clostridium difficile*, wherein said monoclonal antibody is not cross-reactive with Toxin A of *Clostridium difficile*.

4. The hybridoma of claim 3 wherein said hybridoma is selected from the group consisting of 5C8, 5A2, 7D8, 5A8, and 1D5.

5. A method for detecting the presence of *Clostridium difficile* Toxin B in a sample comprising contacting said sample with a monoclonal antibody specific for *Clostridium difficile* Toxin B; and detecting the binding of said antibody to *Clostridium difficile* Toxin B.

6. The method according to claim 5, wherein said antibody is labeled.

7. The method according to claim 5, wherein said antibody is attached to a solid support.

8. The method according to claim 5, wherein said sample is a biological sample.

9. The method according to claim 8, wherein said sample is a stool sample.

* * * * *

UNITED STATES PATENT AND TRADEMARK OFFICE
CERTIFICATE OF CORRECTION

PATENT NO. : 5,231,003

DATED : July 27, 1993

INVENTOR(S) : Richard T. Coughlin, et al

It is certified that error appears in the above-identified patent and that said Letters Patent is hereby corrected as shown below:

Column 12, line 19, after "respectively." insert --Cell lines 7D8, 5C8 and 1D5 were deposited with the American Type Culture Collection, Rockville, Maryland, on January 19, 1993 and given the designation HB 11237, HB 11238, and HB 11241, respectively.--

Signed and Sealed this

Fifth Day of July, 1994

Attest:

BRUCE LEHMAN

Attesting Officer

Commissioner of Patents and Trademarks